United States Patent
Hartman et al.

(10) Patent No.: US 6,361,772 B1
(45) Date of Patent: Mar. 26, 2002

(54) HUMAN MANGANESE SUPEROXIDE DISMUTASE DNA, ITS EXPRESSION AND METHOD OF RECOVERING HUMAN MANGANESE SUPEROXIDE DISMUTASE

(75) Inventors: Jacob R. Hartman, Holon; Yaffa Beck, Gadera, both of (IL)

(73) Assignee: Bio-Technology General Corp., New York, NY (US)

( * ) Notice: Subject to any disclaimer, the term of this patent is extended or adjusted under 35 U.S.C. 154(b) by 342 days.

(21) Appl. No.: 08/686,466

(22) Filed: Jul. 25, 1996

Related U.S. Application Data

(63) Continuation of application No. 08/370,461, filed on Jan. 9, 1995, now Pat. No. 5,540,911, which is a continuation of application No. 08/120,951, filed on Sep. 14, 1993, now abandoned, which is a division of application No. 07/912, 213, filed on Jul. 10, 1992, now Pat. No. 5,270,195, which is a continuation of application No. 07/453,057, filed on Dec. 13, 1989, now abandoned, which is a continuation of application No. 07/032,734, filed on Mar. 27, 1987, now abandoned, which is a continuation-in-part of application No. 06/907,051, filed on Sep. 12, 1986, now abandoned, which is a continuation-in-part of application No. 06/801, 090, filed on Nov. 22, 1985, now abandoned.

(30) Foreign Application Priority Data

Oct. 29, 1986 (IE) .............................. 2851/86

(51) Int. Cl.[7] ............................................ A61K 38/44
(52) U.S. Cl. ................................................. 424/94.4
(58) Field of Search ........................ 424/94.4; 435/189

(56) References Cited

U.S. PATENT DOCUMENTS

| | | | |
|---|---|---|---|
| 3,920,521 A | 11/1975 | Michelson et al. ............ | 195/55 |
| 4,129,644 A | 12/1978 | Kalopissis et al. ............ | 424/54 |
| 4,425,437 A | 1/1984 | Riggs .......................... | 435/317 |
| 4,517,294 A | 5/1985 | Bock et al. .................... | 435/70 |
| 4,563,349 A | 1/1986 | Miyata et al. ................. | 424/94 |
| 4,695,456 A | 9/1987 | Wilder ....................... | 424/94.5 |
| 4,742,004 A | 5/1988 | Hartman et al. .............. | 435/20 |
| 4,751,180 A | 6/1988 | Cousens et al. ............... | 435/68 |
| 5,240,847 A | 8/1993 | Heckl et al. ................. | 435/189 |
| 5,260,204 A | 11/1993 | Heckl et al. ................. | 435/189 |

FOREIGN PATENT DOCUMENTS

| | | |
|---|---|---|
| BE | 905796 | 12/1986 |
| EP | 0131843 | 1/1985 |
| EP | 0138111 | 4/1985 |
| EP | 0196056 | 10/1986 |
| EP | 0213628 | 3/1987 |
| WO | WO 8701387 | 3/1987 |

OTHER PUBLICATIONS

Bannister et al., Methods in Enzymology 105, pp. 88–93 (1984).
Baret et al., Biochemical Pharmacology 33(17), pp. 2755–2760 (1984).
Barra et al., Proceedings of the Third Int'Conf. on Superoxide and SOD, vol. 1, pp. 336–339, Elsevier Science Publishing Co. (1983).
Barra et al., Chemical Abstracts 100: 19771g (1984).
Barra et al., J. Biol. Chem. 259: 12595–12601 (1984).
Barra et al., FEBS Letters 120: 53–56 (1980).
Beck et al, Nucleic Acids Res. 15(21): 9076 (Nov. 11, 1987).
Beyer et al., The Journal of Biological Chemistry 262(23), pp. 11182–11187 (Aug. 1987).
Briggs et al., Toxicology Letters 27, pp. 91–96 (1985).
Coombs, Dictionary of Biotechnology, Elsevier, New York, p. 248 (1986).
Crapo et al., Methods of Enzymology 53, pp. 382–393 (1978).
Cunningham et al., Cancer Letters 21: 149–153 (1983).
Dayoff, Atlas of Protein Sequence and Structure, vol. 5 (1972), National Biomedical Research Foundation, pp. 76, 78 and 79.
Freifelder, Molecular Biology, Jones and Bartlett Publishers, Boston, MA, pp. 826–833 (1983).

(List continued on next page.)

*Primary Examiner*—Charles L. Patterson, Jr.
(74) *Attorney, Agent, or Firm*—John P. White; Cooper & Dunham LLP

(57) ABSTRACT

A double-stranded cDNA molecule which includes DNA encoding human manganese superoxide dismutase has been created. The sequence of one strand of a double-stranded DNA molecule which encodes human manganese superoxide dismutase has been discovered. Such molecules may be introduced in procaryotic, e.g., bacterial, or eukaryotic, e.g., yeast or mammalian, cells and the resulting cells cultured or grown under suitable conditions so as to produce human manganese superoxide dismutase or analogs thereof which may then be recovered. By this invention, human MnSOD gene fragments from various plasmids may be ligated to yield a complete genomic human MnSOD gene fragment. Human MnSOD or analogs thereof may be used to catalyze the reduction of superoxide radicals, reduce reperfusion injury, prolong the survival time of isolated organs, or treat inflammations.

The invention also concerns a method of producing enzymatically active human manganese superoxide dismutase or an analog thereof in a bacterial cell which contains and is capable of expressing a DNA sequence encoding the superoxide dismutase by maintaining the bacterial cell under suitable conditions and in a suitable production medium. The production medium is supplemented with an amount of $Mn^{++}$ so that the concentration of $Mn^{++}$ in the medium is greater than about 2 ppm. Genomic MnSOD DNA should also be capable of expression in eucaryotic cells under suitable conditions.

This invention also concerns a method of recovering purified enzymatically active manganese superoxide dismutase from bacterial cells. It should also be possible to recover manganese SOD from genomic MnSOD DNA expressed in eucaryotic cells using similar methods.

4 Claims, 9 Drawing Sheets

OTHER PUBLICATIONS

Gorecki et al., Free. Rad. Res. Comms. Vols. 12–13, pp. 401–410 (1991).

Harris et al., Eur. J. Biochem. 106, pp. 297–303 (1980).

Lehninger, Principles of Biochemistry,. Worth Publishers, 1982, p. 918.

Lieman–Hurwitz et al., P.N.A.S. 79: 2808–2811 (May 1982).

Marklund, P.N.A.S. 79, pp. 7634–7638 (1982).

Marres et al., Eur. J. Biochem 147: 153–161 (1985).

McCord et al., J. Biol. Chem. 244(22): 6049–6055 (1969).

McCord et al., Movement, Metabolism and Bactericidal Mechanisms of Phagocytes, pp. 257–264 (1977).

Michelson et al., Superoxide and Superoxide Dismutases, 1977, Academic Press, London, pp. 129–138 and 225–230.

Nimrod et al., Frontiers of reactive oxygen species in biology and medicine, 1994, pp. 383–387.

Nimrod et al., Medical Biochemical and Chemical Aspects of Free Radicals, Kyoto, Proceedings of the 4th Biennial Meeting of the Society for Free Radical Research, Japan, Apr. 9–13, 1988, pp. 743–746.

Oberley et al., Cancer Research 39: 1141–1149 (1979).

Ohno et al., Chem. Abstracts 100, abstract No. 17346y: corresponding full length paper (1983) also enclosed.

Omar et al., Free Radical Biology & Medicine 9, pp. 473–478 (1990).

Parizada et al. Free Rad. Res. Comms. 15, pp. 297–301 (1991).

Steinman, Superoxide Dismutase (Oberley, ed.), CRC Press, Florida, 1982, pp. 11–68.

Stryer, Biochemistry, W.H. Freemand & Co., San Fransisco, p. 18 (1975).

Suggs et al., P.N.A.S. 78 (11): 6613–6617 (1981).

Suzuki et al., An Introduction to Genetic Analysis, Third Edition, W.H. Freeman and Company, New York (1986), pp. 133 and 140.

Takeda et al., Nucleic Acids Res. 14(11): 4577–4589 (1986).

Touati, J. of Bacteriology 153(3): 1078–1087 (1983).

Watson et al., Recombinant DNA–A short course, Scientific American Books (1983). p. 78.

Wong et al., Science 242, pp. 941–944 (1988).

FIGURE 1

```
              10         20         30         40         50         60
               *          *          *          *          *          *
GAA TTC GGC GGC GGC ATC AGC GGC TAA GCC AGC ACT AGC AGC ATG TTG AGC CGG GCA GTG
                                                    Met Leu Ser Arg Ala Val 70         80         90        100        110        120
               *          *          *          *          *          *
TGC GGC ACC AGC AGG CAG CTG GCT CCG GCT TTG GGG TAT CTG GGC TCC AGG CAG AAG CAC
Cys Gly Thr Ser Arg Gln Leu Ala Pro Ala Leu Gly Tyr Leu Gly Ser Arg Lgn Lys His 130        140        150        160        170        180
               *          *          *          *          *          *
AGC CTC CCC GAC CTG CCC TAC GAC TAC GGC GCC CTG GAA CCT CAC ATC AAC GCG CAG ATC
Ser Leu Pro Asp Leu Pro Tyr Asp Tyr Gly Ala Leu Glu Pro His Ile Asn Ala Gln Ile 190        200        210        220        230        240
               *          *          *          *          *          *
ATG CAG CTG CAC CAC AGC AAG CAC CAC GCG GCC TAC GTG AAC AAC CTG AAC GTC ACC GAG
Met Gln Leu His His Ser Lys His His Ala Ala Tyr Val Asn Asn Leu Asn Val Thr Glu 250        260        270        280        290        300
               *          *          *          *          *          *
GAG AAG TAC CAG GAG GCG TTC GCC AAG GGA GAT GTT ACA GCC CAG ATA GCT CTT CAG CCT
Glu Lys Tyr Gln Glu Ala Leu Ala Lys Gly Asp Val Thr Ala Gln Ile Ala Leu Gln Pro 310        320        330        340        350        360
               *          *          *          *          *          *
GCA CTG AAG TTC AAT GGT GGT GGT CAT ATC AAT CAT AGC ATT TTC TGG ACA AAC CTC AGC
Ala Leu Lys Phe Asn Gly Gly Gly His Ile Asn His Ser Ile Phe Trp Thr Asn Leu Ser 370        380        390        400        410        420
               *          *          *          *          *          *
CCT AAC GGT GGT GGA GAA CCC AAA GGG GAG TTG CTG GAA GCC ATC AAA CGT GAC TTT GGT
Pro Asn Gly Gly Gly Glu Pro Lys Gly Glu Leu Leu Glu Ala Ile Lys Arg Asp Phe Gly 430        440        450        460        470        480
               *          *          *          *          *          *
TCC TTT GAC AAG TTT AAG GAG AAG CTG ACG GCT GCA TCT GTT GGT GTC CAA GGC TCA GGT
Ser Phe Asp Lys Phe Lys Glu Lys Leu Thr Ala Ala Ser Val Gly Val Gln Gly Ser Gly 490        500        510        520        530        540
               *          *          *          *          *          *
TGG GGT TGG CTT GGT TTC AAT AAG CAA CGG GGA CAC TTA CAA ATT GCT GCT TGT CCA AAT
Trp Gly Trp Leu Gly Phe Asn Lys Gln Arg Gly His Leu Gln Ile Ala Ala Cys Pro Asn 550        560        570        580        590        600
               *          *          *          *          *          *
CAG GAT CCA CTG CAA GGA ACA ACA GGC CTT ATT CCA CTG CTG GGG ATT GAT GTG TGG GAG
Gln Asp Pro Leu Gln Gly Thr Thr Gly Leu Ile Pro Leu Leu Gly Ile Asp Val Trp Glu 610        620        630        640        650        660
               *          *          *          *          *          *
CAC GCT TAC TAC CTT CAG TAT AAA AAT GTC AGG CCT GAT TAT CTA AAA GCT ATT TGG AAT
His Ala Tyr Tyr Leu Gln Tyr Lys Asn Val Arg Pro Asp Tyr Leu Lys Ala Ile Trp Asn 670        680        690        700        710        720
               *          *          *          *          *          *
GTA ATC AAC TGG GAG AAT GTA ACT GAA AGA TAC ATG GCT TGC AAA AAG TAA ACC ACG ATC
Val Ile Asn Trp Glu Asn Val Thr Glu Arg Tyr Met Ala Cys Lys Lys ---

730        740        750        760        770        780
               *          *          *          *          *          *
GTT ATG CTG ATC ATA CCC TAA TGA TCC CAG CAA GAT AAT GTC CTG TCT TCT AAG ATG TGC 790        800        810
               *          *          *
ATC AAG CCT GGG TAC ATA CTG AAA CCC CGA ATT
```

FIGURE 6

Nucleotide Sequence of Human MnSOD Gene

```
   1 AACCAAAAAC TCACGGGGCC AGCGCCGGCA GGGCCGCCTA GTGCAGCCAG ATCCCCGCCG
  61 GCACCTCAGG GGGCGGACCC GCAGGCAGGG CTTGCGGGCC GTACCAACTG CCACGGGGGC
 121 AGGGGCCGCC TCCCTTCGGC CGCGCGCCAC TGCAAGTACG GCAGGACACC AGCGAGGTTG
 181 CCGAGGCCGA GGCTAGCCTG CAGCCTCCTT TCTCCCGTGC CCTGGGCGCG GGTGTACGG
 241 CAAGCGCGGG CGGGCGGGAC AGGCACGCAG GGCACCCCCG GGGTTCGGGC GCGGCGGGCG
 301 GGGCGGGGC TCGCGGGGGG AGGGGCCGG GCGGCGGTCG CCCTTGTCGG CGCAGCTGGG
 361 TCGCGGCCCT GCTCCCGGCG CTTTCTTAAG GCCCGCGGGC GGCGCAGGAG CGGTCACTCG
 421 TGGCTGTGGT GGCTTCGGCA GCGGCTTCAG CAGATCGGCG GCATAGGGG AAGCCAGCA
 481 CTAGCAGCAT GTTGAGCCGG GCAGTGTGCG GGTGAGAAGG AAGGGGACCC GGTCACGCCC
 541 CAAGGGGAAG GGGCTCGCGG CGGGCAGGGC TCCGGGCAAT GGCGACATGG CCGCACGGGC
 601 CTGGCGGGAC CGCCGACCTG CAGGCGGTTC TCCCGGGAGT GCCCCGCGCG GCGGCCTCGA
 661 GCCGGGGATC CGAGGGAGGG GACGCGGGGA CTCGGGGGAC GCCGCGCTGC GTTCCTCGGC
 721 AGCCCAGCCT GCGTAGACGG TCCGCGGCGC TGACTGACCG GGCTGTGCTT TCTCGTCTTC
 781 AGGCACCAGC AGGCAGCTGG TCTCCGGTTT GGGGTATCTG GGCTCCAGGC AGAAGCACAG
 841 CCTCCCCAG GTGCCCTACG AGTACGGCGC CTGGAACCT CACATCAACG GGCAGATCAT
 901 GCAGCTGCAC GACAGCAAGC ACCACGCGGC CTACGTCAAC AACCTGAACG TCACCGAGGA
 961 GAAGTACCAG GAGGCGTTGG CCAAGGGTAG GTTCCAGGCT GAGCGGG...
1021 AAAAAAATGT GGTTTGCACT TTTAACTTTT AAGGAGATGT TACAGCCCAG AAGCTCTT
1081 AGCCTGCACT GAAGTTCAAT GGTGGTGGTC ATATCAATCA TAGCATTTTG GGACAAACG
1141 TCAGCCCTAA GGGTGGTGGA GAACCCAAAG GTTGGATATA TTGTGCACCC TTATCTACAA
1201 CTTCTTGCAC AGTAGGAATC GAT.......
1261 GTAATTTCTT GGGCCCTATG ACAAAAAATA TTTTGAATAC ATGTAATATA ACATTTTACT
1321 GTAATTATTG GAAATCTGTT CATTTGTGGG TGGTTTTGGG ATTTTTTTTT TAATAGGGG
1381 GTTGCTGGAA GCCATCAAAC GTGACTTTGG TCCCTTGAG AAGGTAAGG AGAAGCTGAC
1441 GGCTGCATCT GTTGGTGTCC AAGGCTCAGG GTGGGGTTGG GTTGGTTCA ATAAGCAACG
1501 GGGACACGTA CAAATTGCTG CTTGTCCAAA TCAGGATCCA CTGCAAGGAA CAACAGTTA
1561 CATTTAGATA GGGTTGAGTG TTGTTCCAGT TTGGAAAACG AGTCCACTAT TAAAGAACGT
1621 GGACTCCAAC GTCAAAGGGC GAAAAACCGT CTATCAGGGC GATGGCCACT ACGTGAACCA
1681 TCACCCAAAT CAAGTTTTTT GGGGTCGAGG TGCCGTGAAA GCACTAAATC GGAACCTAAA
1741 GGGAGCCCCC GATTTAGAGC TTGACGGGGA AAGCCGGCG AACTGTGGCG AGAAAGGAAG
1801 GGAAGAAAGC GAAAGGAGCG GCGCTAGGC GTGGCAATTG TGTAGCGTCA CTGGCG....
1861 CCCCCTTCTT TCTAACAGGC CTTATTCCAC TGCGGGAT TGATGTGCA TAGCAGCGT
1921 ACTACCTTCA GTATAAAAT GTCAGCCCTG ATTATGTAAA AGCTATTTGG AATGTAATCA
1981 AGTGGGAGAA TGTAACTGAA AGATACATGG CTTGCAAAAA GTAAACCACG ATGGTTATGG
2041 TGAGTATGTT AAGCTCTTTA TGACTGACTA TGTAGTGGTA TAGAGTACTG CAG......
2101 GTCCATATCT AAAACCACGT ATAAACATTA AATTGTATTT CCTGTTTTAA TTCCAGGGGA
2161 AGTACTGTTT GGGAAAGCTA TTATTAGGTA AATGTTTTAC AAATTACTGT TTCTCAGTTT
2221 CAGTCATACC CTAATGATCC CAGCAAGATA ATGTCCTGTC TTCTAAGATG GCATCAAGG
2281 CTGGGTACAT ACTGAAACCC TATAAGGTCC CTGGATAATT TTTGTTTGAT TATTGCATTG
2341 AAGAAACATT TATTTTCCAA AATTGTGTGA AGTTTTTGAC TGTTAATAAA AGAATCTGTC
2401 AACCATCAAA GAGGTCTGCA TTAATGCTTG CATGTCTTTT TCATTAAAAA TCCTATAATC
2461 TTCTGTCATT TTCACTGAGT TTCCATGGGA AAGGAATAGT AAACTAATGG GTAGTTGAAA
2521 TATTACTCTT AAGACCAAGA CCTGTGTCTC CAGTCATATC TGTAATAACA TCATCTGATA
2581 ACCTAAAAGC ATAGTATTAG GGATATACGA CAAAACCAAA GTGTTTTTGC TGTTGTCACA
2641 TACCACTCAA TACTTTTACA CCAGTTTGTC CAGTGGGACT CCAGCTG... ..........
```

FIGURE 7

|  | EXON | INTRON | EXON |
|---|---|---|---|
| INTRON #1 | TGTGCG | GGTGAG...CTTCAG | GCACCA |
| INTRON #2 | CCAAGG | GTAGGT...TTTAAG | GAGATG |
| INTRON #3 | CCAAAG | GTTGGA...TAATAG | GGGAGT |
| INTRON #4 | CAACAG | GTTACA...TAACAG | GCCTTA |
| INTRON #5 | TGCTGA | GTATGT...TTTCAG | TCATAC |

| CONSENSUS | AG | GT AGT... NCAG | G |
|---|---|---|---|

Consensus variants:
- Position 3 of intron start: A or G (below GT)
- Position 2-3 before intron end: TT or CC

HUMAN MANGANESE SUPEROXIDE DISMUTASE DNA, ITS EXPRESSION AND METHOD OF RECOVERING HUMAN MANGANESE SUPEROXIDE DISMUTASE

This application is a continuation of U.S. Ser. No. 08/370,461, filed Jan. 9, 1995, now U.S. Pat. No. 5,540,911, issued Jul. 30, 1996; which is a continuation of U.S. Ser. No. 08/120,951, filed Sep. 14, 1993, now abandoned; which is a divisional of U.S. Ser. No. 07/912,213, filed Jul. 10, 1992, now U.S. Pat. No. 5,270,195, issued Dec. 14, 1993; which is a continuation of U.S. Ser. No. 07/453,057, filed Dec. 13, 1989, now abandoned; which is a continuation of U.S. Ser. No. 07/032,734, filed Mar. 27, 1987, now abandoned; which was a continuation-in-part of Ser. No. 06/907,051, filed Sep. 12, 1986, now abandoned; which was a continuation-in-part of Ser. No. 06/801,090, filed Nov. 22, 1985, now abandoned.

BACKGROUND OF THE INVENTION

Throughout this application, various publications are referenced by arabic numerals within parentheses. Full citations for these references may be found at the end of the specification immediately preceding the claims. The disclosures of these publications in their entireties are hereby incorporated by reference into this application in order to more fully describe the state of art as known to those skilled therein as of the date of the invention described and claimed herein.

Superoxide dismutase (SOD) and the phenomenon of oxygen free radicals ($O_2 \cdot$) was discovered in 1968 by McCord and Fridovich (1). Superoxide radicals and other highly reactive oxygen species are produced in every respiring cell as by-products of oxidative damage to a wide variety of macromolecules and cellular components (for review see 2,3). A group of metalloproteins known as superoxide dismutases catalyze the oxidation-reduction reaction $2O_2 \cdot + 2H^+ \rightarrow H_2O_2 + O_2$ and thus provide a defense mechanism against oxygen toxicity.

There are several known forms of SOD containing different metals and different proteins. Metals present in SOD include iron, manganese, copper and zinc. All of the known forms of SOD catalyze the same reaction. These enzymes are found in several evolutionary groups. Superoxide dismutases containing iron are found primarily in prokaryotic cells. Superoxide dismutases containing copper and zinc has been found in virtually all eukaryotic organisms (4). Superoxide dismutases containing manganese have been found in organisms ranging from microorganisms to man.

Since every biological macromolecule can serve as a target for the damaging action of the abundant superoxide radical, interest has evolved in the therapeutic potential of SOD. The scientific literature suggests that SOD may be useful in a wide range of clinical applications. These include prevention of oncogenesis and of tumor promotion, and reduction of the cytotoxic and cardiotoxic effects of anti-cancer drugs (10), protection of ischemic tissues (12) and protection of spermatozoa (13). In addition, there is interest in studying the effect of SOD on the aging process (14).

The exploration of the therapeutic potential of human SOD has been limited mainly due to its limited availability.

Superoxide dismutase is also of interest because of its anti-inflammatory properties (11). Bovine-derived superoxide dismutase (orgotein) has been recognized to possess anti-inflammatory properties and is currently marketed in parts of Europe as a human pharmaceutical.

It is also sold in the United States as a veterinary product, particularly for the treatment of inflamed tendons in horses. However, supplies of orgotein are limited. Prior techniques involving recovery from bovine or other animal cells have serious limitations and the orgotein so obtained may produce allergic reactions in humans because of its non-human origin.

Copper zinc superoxide dismutase (CuZn SOD) is the most studied and best characterized of the various forms of superoxide dismutase.

Human CuZn SOD is a dimeric metallic-protein composed of identical non-covalently linked subunits, each having a molecular weight of 16,000 daltons and containing one atom of copper and one of zinc (5). Each subunit is composed of 153 amino acids whose sequence has been established (6,7).

The cDNA encoding human CuZn superoxide dismutase has been cloned (8). The complete sequence of the cloned DNA has also been determined (9). Moreover, expression vectors containing DNA encoding superoxide dismutase for the production and recovery of superoxide dismutase in bacteria have been described (24,25). The expression of a superoxide dismutase DNA and the production of SOD in yeast has also been disclosed (26).

Recently, the CuZn SOD gene locus on human chromosome 21 has been characterized (27) and recent developments relating to CuZn superoxide dismutase have been summarized (28).

Much less is known about manganese superoxide dismutase (MnSOD). The MnSOD of *E. coli* K-12 has recently been cloned and mapped (22). Barra et al. disclose a 196 amino acid sequence for the MnSOD polypeptide isolated from human liver cells (19). Prior art disclosures differ, however, concerning the structure of the MnSOD molecule, particularly whether it has two or four identical polypeptide subunits (19,23). It is clear, however, that the MnSOD polypeptide and the CuZn SOD polypeptide are not homologous (19). The amino acid sequence homologies of MnSODs and FeSOD from various sources have also been compared (18).

Baret et al. disclose in a rat model that the half life of human MnSOD is substantially longer than the half-life of human copper SOD; they also disclose that in the rat model, human MnSOD and rat copper SOD are not effective as anti-inflammatory agents whereas bovine copper SOD and human copper SOD are fully active (20).

McCord et al. disclose that naturally occurring human manganese superoxide dismutase protects human phagocytosing polymorphonuclear (PMN) leukocytes from superoxide free radicals better than bovine or porcine CuZn superoxide dismutase in "in vitro" tests (21).

The present invention concerns the preparation of a cDNA molecule encoding the human manganese superoxide dismutase polypeptide or an analog or mutant thereof. It is also directed to inserting this cDNA into efficient bacterial expression vectors, to producing human MnSOD polypeptide, analog, mutant and enzyme in bacteria, to recovering the bacterially produced human MnSOD polypeptide, analog, mutant or enzyme. This invention is also directed to the human MnSOD polypeptides, analogs, or mutants thereof so recovered and their uses.

This invention further provides a method for producing enzymatically active human MnSOD in bacteria, as well as a method for recovering and purifying such enzymatically active human MnSOD.

The present invention also relates to a DNA molecule encoding the human MnSOD gene. It is also directed to inserting the DNA into mammalian cells to produce MnSOD polypeptide, analog, mutant and enzyme.

The present invention also relates to using human manganese superoxide dismutase or analogs or mutants thereof to catalyze the reduction of superoxide radicals to hydrogen peroxide and molecular oxygen. In particular, the present invention concerns using bacterially produced MnSOD or analogs or mutants thereof to reduce reperfusion injury following ischemia and prolong the survival period of excised isolated organs. It also concerns the use of bacterially produced MnSOD or analogs thereof to treat inflammations.

SUMMARY OF THE INVENTION

A DNA molecule which includes cDNA encoding the human manganese superoxide dismutase polypeptide or analog or mutant thereof has been isolated from a human T-cell library. The nucleotide sequence of a double-stranded DNA molecule which encodes human manganese superoxide dismutase polypeptide or analog or mutant thereof has been discovered. The sequence of one strand encoding the polypeptide or analog thereof is shown in FIG. 1 from nucleotide 115 downstream to nucleotide 708 inclusive. Other sequences encoding the analog or mutant may be substantially similar to the strand encoding the polypeptide. The nucleotide sequence of one strand of a double stranded DNA molecule which encodes a twenty-four (24) amino acid prepeptide is also shown in FIG. 1, from nucleotides number 43 through 114, inclusive.

The double-stranded cDNA molecule or any other double-stranded DNA molecule which contains a nucleotide strand having the sequence encoding the human manganese superoxide dismutase polypeptide or analog or mutant thereof may be incorporated into a cloning vehicle such as a plasmid or virus. Either DNA molecule may be introduced into a cell, either procaryotic, e.g., bacterial, or eukaryotic, e.g., yeast or mammalian, using known methods, including but not limited to methods involving cloning vehicles containing either molecule.

Preferably the cDNA or DNA encoding the human manganese superoxide dismutase polypeptide or analog or mutant thereof is incorporated into a plasmid, e.g., pMSE-4 or pMSΔRB4, and then introduced into a suitable host cell where the DNA can be expressed and the human manganese superoxide dismutase (hMnSOD) polypeptide or analog or mutant thereof produced. Preferred host cells include *Escherichia coli,* in particular *E. coli* A4255 and *E. coli* A1645. The plasmid pMSE-4 in *E. coli* strain A4255 has been deposited with the American Type Culture Collection under ATCC Accession No. 53250. The plasmid pMS RB4 may be obtained as shown in FIG. 4 and described in the Description of the Figures.

Cells into which such DNA molecules have been introduced may be cultured or grown in accordance with methods known to those skilled in the art under suitable conditions permitting transcription of the DNA into mRNA and expression of the mRNA as protein. The resulting manganese superoxide dismutase protein may then be recovered.

Veterinary and pharmaceutical compositions containing human MnSOD or analogs or mutants thereof and suitable carriers may also be prepared. This human manganese superoxide dismutase or analogs or mutants may be used to catalyze the following reaction:

$$2O_2^{\cdot-} + 2H^+ \rightarrow H_2O_2 + O_2$$

and thereby reduce cell injury caused by superoxide radicals.

More particularly, these enzymes or analogs or mutants thereof may be used to reduce injury caused by reperfusion following ischemia, increase the survival time of excised isolated organs, or treat inflammations.

This invention is directed to a method of producing enzymatically active human manganese superoxide dismutase or an analog or mutant thereof in a bacterial cell. The bacterial cell contains and is capable of expressing a DNA sequence encoding the manganese superoxide dismutase or analog or mutant thereof. The method comprises maintaining the bacterial cell under suitable conditions and in a suitable production medium. The production medium is supplemented with an amount of $Mn^{++}$ so that the concentration of $Mn^{++}$ available to the cell in the medium is greater than about 2 ppm.

In a preferred embodiment of the invention the bacterial cell is an *Escherichia coli* cell containing a plasmid which contains a DNA sequence encoding for the human manganese superoxide dismutase polypeptide e.g. pMSE-4 or pMSΔRB4 in *E. coli* strain A4255. The concentration of $Mn^{++}$ in the production medium ranges from about 50 to about 1500 ppm, with concentrations of 150 and 750 ppm being preferred.

This invention also concerns a method of recovering manganese superoxide dismutase or analog thereof from bacterial cells which contain the same. The cells are first treated to recover a protein fraction containing proteins present in the cells including human manganese superoxide dismutase or analog or mutant thereof and then the protein fraction is treated to recover human manganese superoxide dismutase or analog or mutant thereof. In a preferred embodiment of the invention, the cells are first treated to separate soluble proteins from insoluble proteins and cell wall debris and the soluble proteins are recovered. The soluble proteins are then treated to separate, e.g. precipitate, a fraction of the soluble proteins containing the hMnSOD or analog or mutant thereof and the fraction containing the hMnSOD or analog or mutant is recovered. The recovered fraction of soluble proteins is then treated to separately recover the human manganese superoxide dismutase or analog thereof.

A more preferred embodiment of the invention concerns a method of recovering human manganese superoxide dismutase or analog or mutant thereof from bacterial cells which contain human manganese superoxide dismutase or analog or mutant thereof. The method involves first isolating the bacterial cells from the production medium and suspending them in suitable solution having a pH of about 7.0 to 8.0. The cells are then disrupted and centrifuged and the resulting supernatant is heated for about 30 to 120 minutes at a temperature between 55 and 65° C., preferably for 45–75 minutes at 58–62° C. and more preferably for 1 hour at 60° C. and then cooled to below 10° C., preferably to 4° C. Any precipitate which forms is to be removed e.g. by centrifugation, and the cooled supernatant is dialyzed against an appropriate buffer e.g. 2 mM potassium phosphate buffer having a pH of about 7.8. Preferably, the dialysis is by ultrafiltration using a filtration membrane smaller than 30K. Simultaneously with or after dialysis the cooled supernatant optionally may be concentrated to an appropriate convenient volume e.g. 0.03 of its original volume. The retentate is then eluted on an anion exchange chromatography column with an appropriate buffered solution e.g. a solution of at least 20 mM potassium phosphate buffer having a pH of about 7.8. The fractions of eluent containing superoxide dismutase are collected, pooled and dialyzed against about 40 mM potassium acetate, pH 5.5.

The dialyzed pooled fractions are then eluted through a cation exchange chromatography column having a linear gradient of about 40 to about 200 mM potassium acetate and a pH of 5.5. The peak fractions containing the superoxide dismutase are collected and pooled. Optionally the pooled peak fractions may then be dialyzed against an appropriate solution e.g. water or a buffer solution of about 10 mM potassium phosphate buffer having a pH of about 7.8.

The invention also concerns purified enzymatically active human manganese superoxide dismutase or analogs thereof e.g. met-hMnSOD, or mutants produced by the methods of this invention.

The present invention also relates to a DNA molecule encoding the human MnSOD gene. The nucleotide sequence of the exon coding regions of one strand of the MnSOD gene is shown in 6. The DNA encoding the MnSOD gene may be incorporated into a cloning vehicle such as a plasmid or a virus. The DNA or the cloning vehicle may be introduced into eucaryotic cells using known methods. Preferably, the DNA encoding the human manganese superoxide dismutase gene is encoded in the plasmids pMSG11-1, pMSG4 and pMSG-1b. The eucaryotic cells which are transformed are preferably mammalian cell lines such as the human HeLa cell line or the mouse L cell line. Another aspect of this invention is the production of the human manganese superoxide dismutase polypeptide, analog, mutant or enzyme by growing the cells of this invention in suitable medium under suitable conditions.

BRIEF DESCRIPTION OF THE FIGURES

FIG. 1. The Sequence of human MnSOD cDNA

FIG. 1 shows the nucleotide sequence of one strand of a double-stranded DNA molecule encoding the human manganese superoxide dismutase as well as the 198 amino acid sequence of human MnSOD corresponding to the DNA sequence. FIG. 1 also shows the nucleotide sequence of one strand of a double stranded DNA molecule encoding a prepeptide to the mature human MnSOD consisting of twenty-four amino acids and the amino acid sequence corresponding to that DNA sequence. Also shown are the 5' and 3' untranslated sequences.

Figure 2:
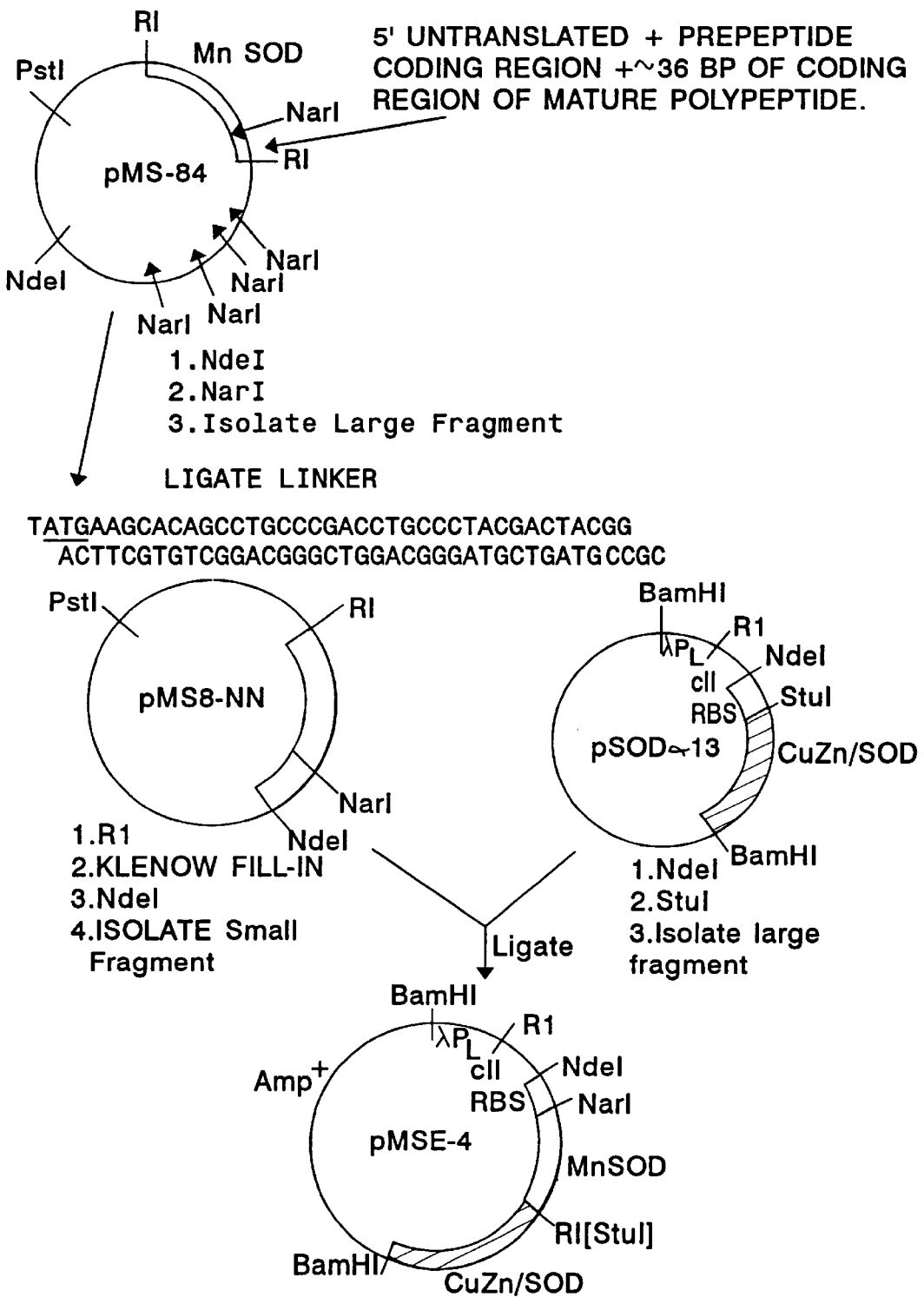
FIG. 2. Construction of pMSE-4: Human MnSOD Expression Plasmid

Plasmid pMS8-4, containing MnSOD on an EcoRI ($R_1$) insert, was digested to completion with NdeI and NarI restriction enzymes. The large fragment was isolated and ligated with a synthetic oligomer as depicted in FIG. 2. The resulting plasmid, pMS8-NN contains the coding region for the mature MnSOD, preceded by an ATG initiation codon. The above plasmid was digested with EcoRI, ends were filled in with Klenow fragment of Polymerase I and further cleaved with NdeI. The small fragment harboring the MnSOD gene was inserted into pSOD 13 which was treated with NdeI and StuI. pSOD-13 may be obtained as described in pending co-assigned U.S. patent application Ser. No. 644,245, filed Aug. 27, 1984 which is hereby incorporated by reference. This generated plasmid pMSE-4 containing the MnSOD coding region preceded by the cII ribosomal binding site and under the control of $\lambda P_L$ promoter. Plasmid pMSE-4 has been deposited with the American Type Culture Collection under ATCC Accession No. 53250.

Figure 3:
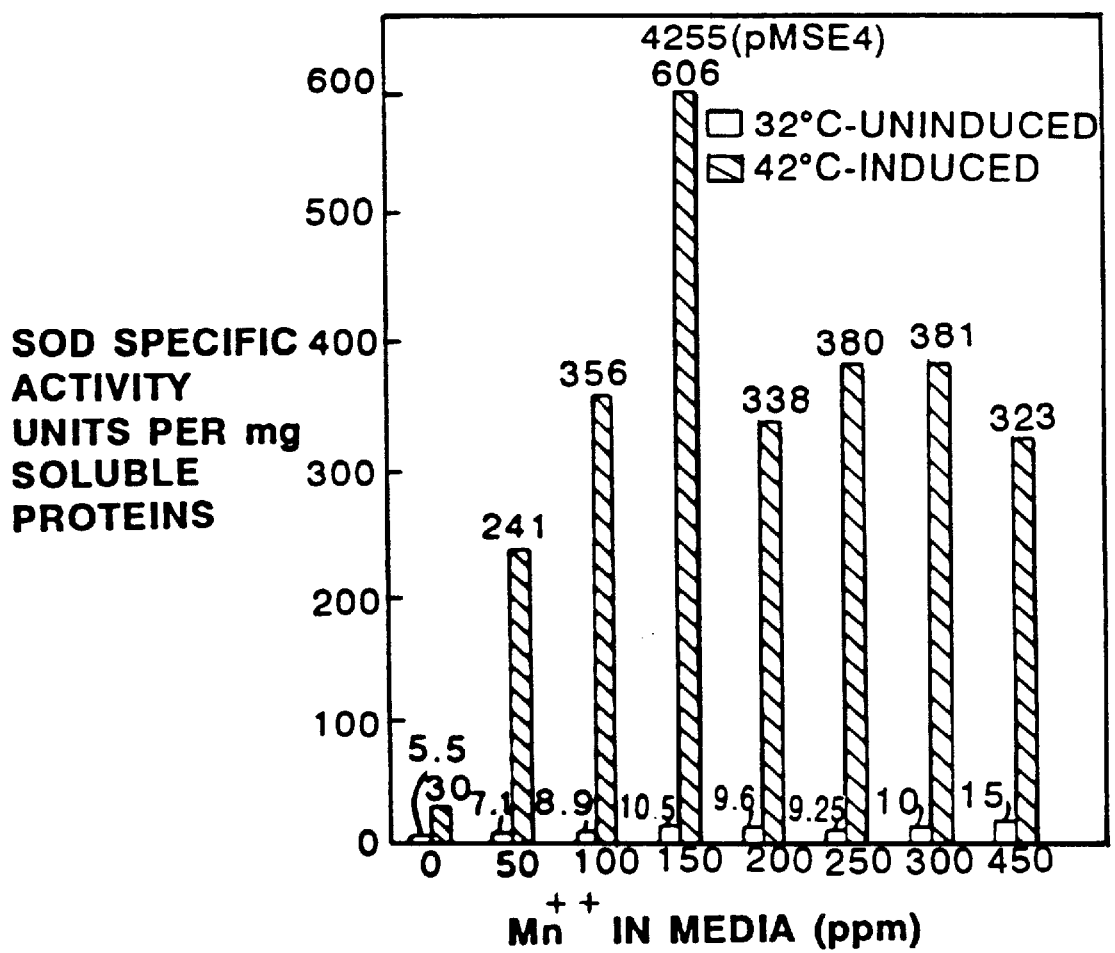

FIG. 3. Effect of $Mn^{++}$ Concentration on the Activity of SOD Produced in *E. Coli*

The chart in FIG. 3 shows the correlation between the specific activity in units/mg of recombinant soluble MnSOD produced by *E. coli* strain A4255 containing plasmid pMSE-4 under both non-induction (32° C.) and induction (42° C.) conditions, and the concentration of $Mn^{++}$ (parts per million) in the growth medium.

Figure 4:
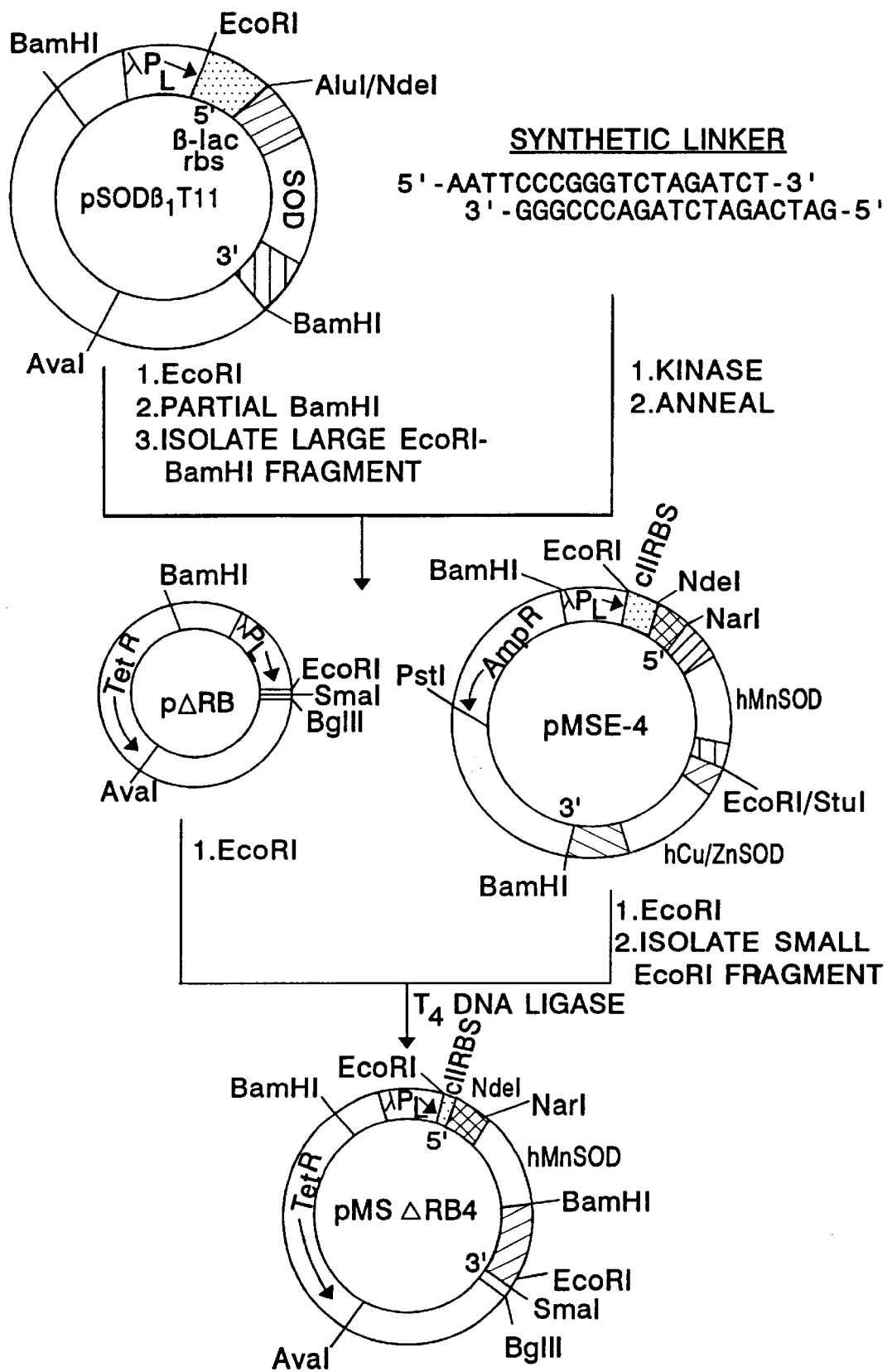

FIG. 4. Construction of pMSΔRB4; Human MnSOD Expression Plasmid $Tet^R$ expression vector, pΔRB, was generated from $pSOD\beta_1$T-11 by complete digestion with EcoRI followed by partial cleavage with BamHI restriction enzymes. $pSOD\beta_1$T-11 has been deposited with the American Type Culture Collection (ATCC) under Accession No. 53468. The digested plasmid was ligated with synthetic oligomer

5'-AATTCCCGGGTCTAGATCT-3'
3'-GGGCCCAGATCTAGACTAG-5' resulting in pΔRB containing the $\lambda P_L$ promoter.

The EcoRI fragment of MnSOD expression plasmid pMSE-4, containing cII ribosomal binding site and the complete coding sequence for the mature enzyme, was inserted into the unique EcoRI site of pΔRB. The resulting plasmid, pMSΔRB4, contains the MnSOD gene under control of $\lambda P_L$ and cII RBS and confers resistance to tetracycline.

Figure 5:
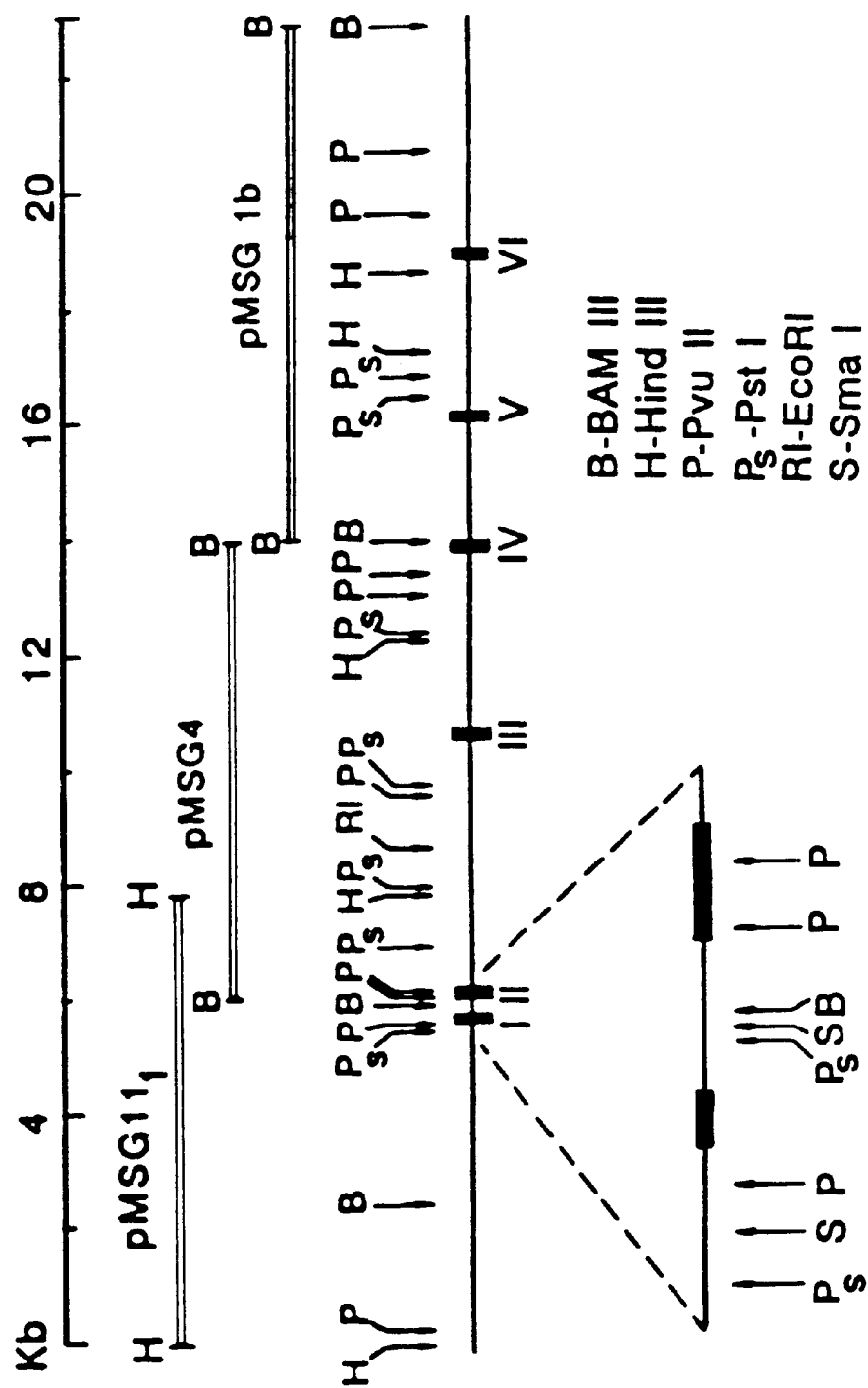

FIG. 5. Restriction Map and Organization of Human MnSOD Gene

The thick line represents genomic DNA with the positions of the various restriction endonucleases. The black boxes numbered I–VI are the exons. The three open bars above represent the genomic clones which contain the MnSOD gene.

FIG. 6. Nucleotide Sequence of Human MnSOD Gene

The coding regions and adjacent nucleotides are shown; the exons (shaded areas) were identified by comparison with the cDNA clones. The initator codon (ATG), termination codon (TAA) and the polyadenylation signal (AATAAA) are underlined. The Spl hexanucleotide (GGGCGG) binding site is indicated by a line above the sequence. Dotted arrows represent possible stem-loop structures; straight arrows are direct repeats. It should be noted that the numbers shown to the left of the Figure are arbitrary and were selected only to assist in the identification of the regions mentioned in the text. Neither the entire non-coding or the entire coding region is shown.

FIG. 7. Exon-Intron Junctions of Human MnSOD Gene

The nucleotide sequence at the borders of all five introns are compared with the consensus sequences. Note that a shift of one nucleotide in intron #1 may alter either the donor or acceptor sequences.

Figure 8:
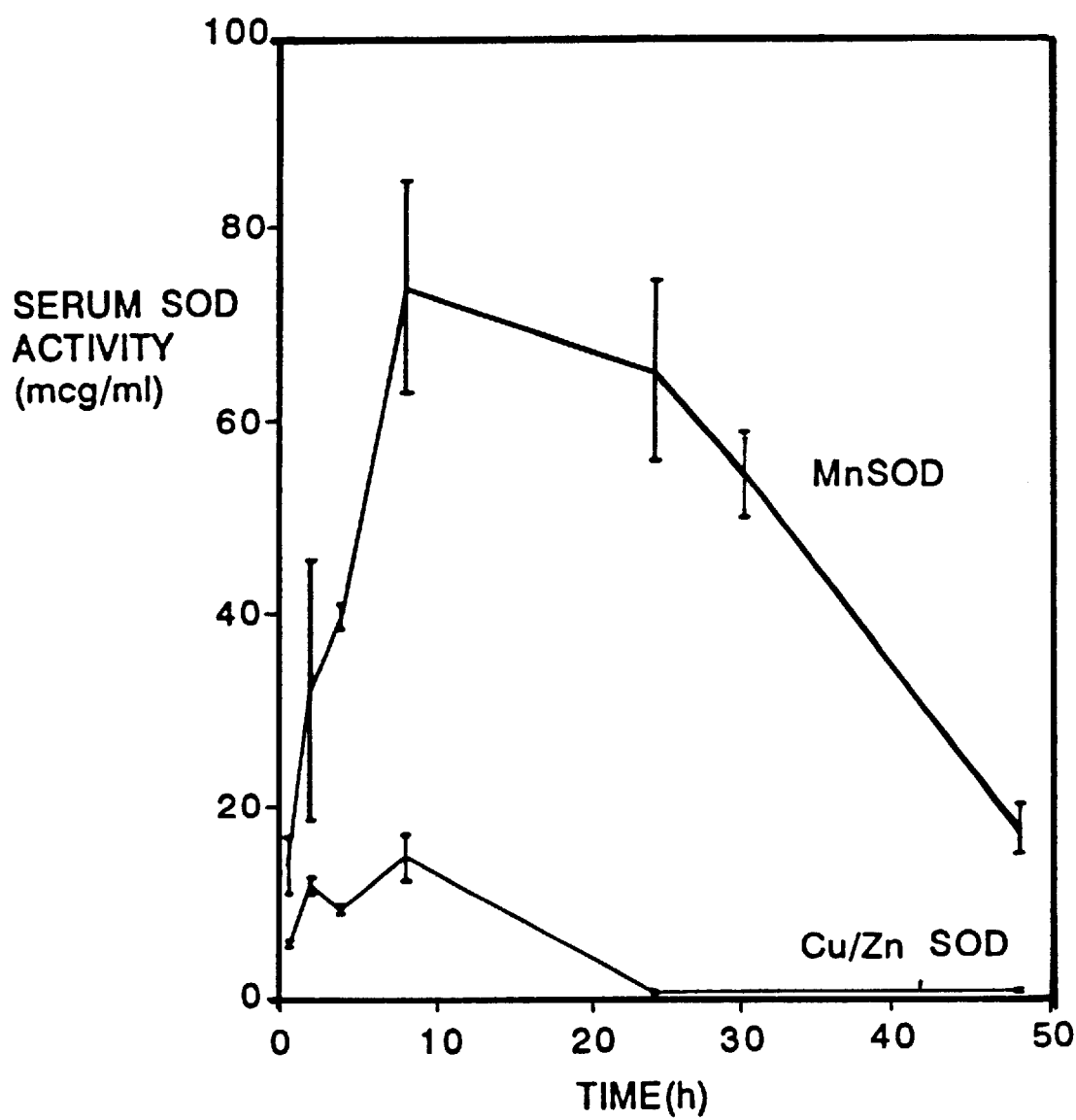

FIG. 8. Pharmacokinetics of MnSOD After Subcutaneous Injection Into Rats

Time course of the serum levels of SOD enzymatic activity in rats after subcutaneous administration of 50 mg/kg of CuZn SOD (lower curve) or MnSOD (upper curve). Values are expressed as the mean and standard error (3 rats per point) of the enzymatic activity, calculated as ug/ml assuming a specific activity of 3000 units/mg.

Figure 9:
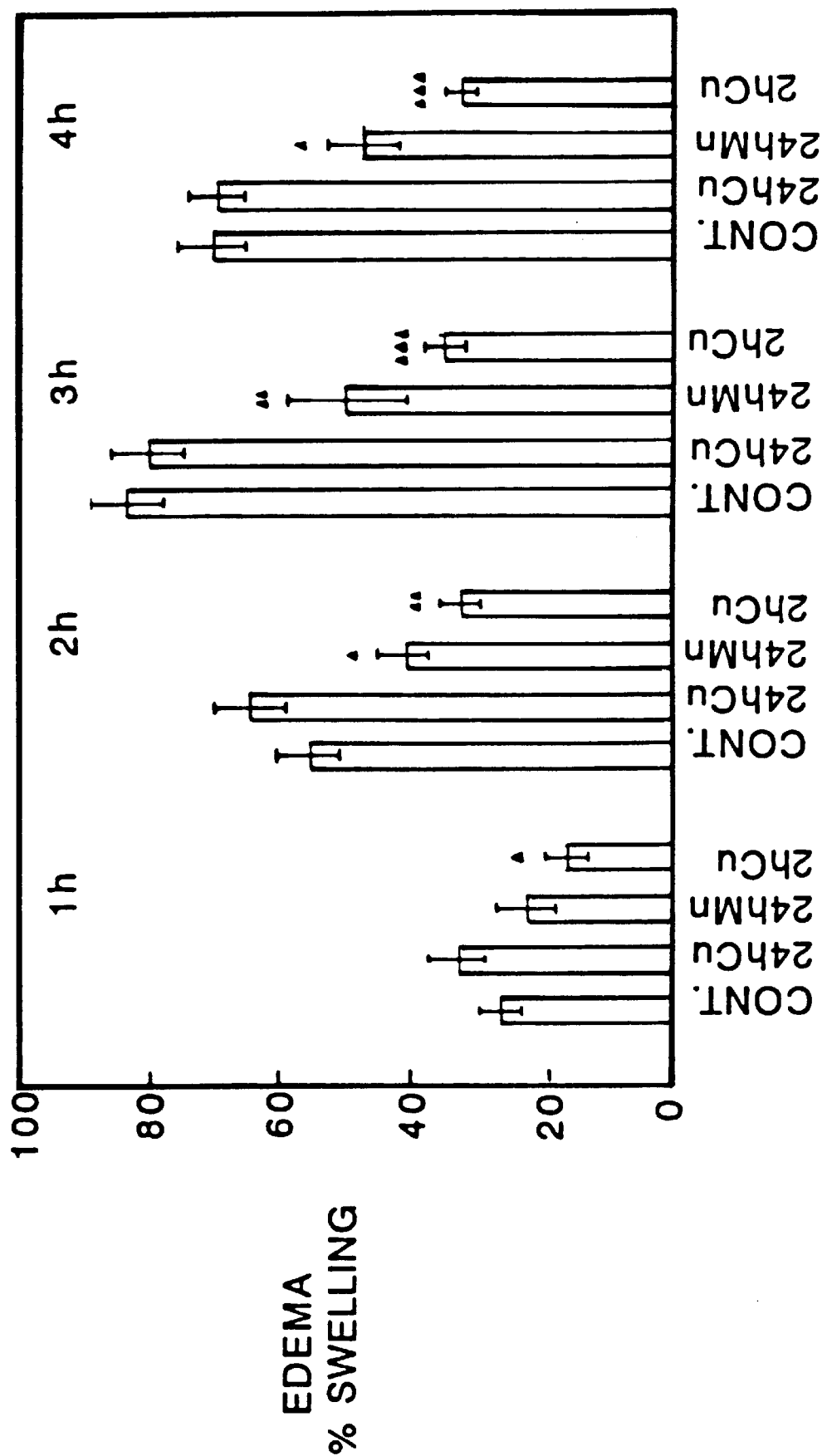

FIG. 9. Comparison Between MnSOD and CuZn SOD

Effect of CuZn SOD and MnSOD administration on carrageenan-induced paw swelling in rats. MnSOD (50 mg/kg) was administered subcutaneously 24 hours before carrageenan injection (−24 h Mn); CuZn SOD (50 mg/kg) was administered subcutaneously 2 hours (−2 h Cu) or 24 hours (−24 h Cu) prior to carrageenan injection. The control rats received carrageenan only. The bars and vertical brackets represent the means±standard errors (8 rats per group) of the increase in paw volume 1, 2, 3 and 4 hours after carrageenan administration. The asterisks indicate the statistical significance of the difference between the treated groups compared to the control group: (*) $p<0.05$; () $p<0.01$; (*) $p<0.001$.

DETAILED DESCRIPTION OF THE INVENTION

A double-stranded DNA molecule which includes cDNA encoding human manganese superoxide dismutase polypeptide or an analog or mutant thereof has been isolated from a human T-cell DNA library. The nucleotide sequence of a double-stranded DNA molecule which encodes human manganese superoxide dismutase polypeptide or an analog or mutant thereof has been discovered. The sequence of one strand of DNA molecule encoding the human manganese superoxide dismutase polypeptide or analog thereof is shown in FIG. 1 and includes nucleotides numbers 115 to 708 inclusive. The sequence of one strand encoding hMn-SOD analog or mutant is substantially similar to the strand encoding the hMnSOD polypeptide. The nucleotide sequence of the prepeptide of human manganese superoxide dismutase is also shown in FIG. 1. Nucleotides numbers 43 through 114 inclusive code for this prepeptide.

The methods of preparing the cDNA and of determining the sequence of DNA encoding the human manganese superoxide dismutase polypeptide, analog or mutant thereof are known to those skilled in the art and are described more fully hereinafter. Moreover, now that the DNA sequence which encodes the human manganese superoxide dismutase has been discovered, known synthetic methods can be employed to prepare DNA molecules containing portions of this sequence.

Conventional cloning vehicles such as plasmids, e.g., pBR322, viruses or bacteriophages, e.g., can be modified or engineered using known methods so as to produce novel cloning vehicles which contain cDNA encoding human manganese superoxide dismutase polypeptide, or analogs or mutants thereof. Similarly, such cloning vehicles can be modified or engineered so that they contain DNA molecules, one strand of which includes a segment having the sequence shown in FIG. 1 for human manganese superoxide dismutase polypeptide or segments substantially similar thereto. The DNA molecule inserted may be made by various methods including enzymatic or chemical synthesis.

The resulting cloning vehicles are chemical entities which do not occur in nature and may only be created by the modern technology commonly described as recombinant DNA technology. Preferably the cloning vehicle is a plasmid, e.g. pMSE-4 or pMSΔRB4. These cloning vehicles may be introduced in cells, either procaryotic, e.g., bacterial (*Escherichia coli, B.subtilis,* etc.) or eukaryotic, e.g., yeast or mammalian, using techniques known to those skilled in the art, such as transformation, transfection and the like. The cells into which the cloning vehicles are introduced will thus contain cDNA encoding human manganese superoxide dismutase polypeptide or analog or mutant thereof if the cDNA was present in the cloning vehicle or will contain DNA which includes a strand, all or a portion of which has the sequence for human MnSOD polypeptide shown in FIG. 1 or sequence substantially similar thereto if such DNA was present in the cloning vehicle.

*Escherichia coli* are preferred host cells for the cloning vehicles of this invention. A presently preferred auxotrophic strain of *E. coli* is A1645 which has been deposited with the American Type Culture Collection in Rockville, Md., U.S.A. containing plasmid pApoE-Ex2, under ATCC Accession No. 39787. All deposits with the American Type Culture Collection referred to in this application were made pursuant to the Budapest Treaty on the International Recognition of the Deposit of Microorganisms.

A1645 was obtained from A1637 by selection for Gal+ (ability to ferment galactose) as well as loss of tetracycline resistance. It still contains elements of phage λ. Its phenotype is C600 r⁻m⁺ gal⁺ thr⁺ leu⁻ lacZ⁻ bl (λcI857 Δ H1 Δ BamH1 N⁺).

A1637 was obtained from C600 by inserting transposon containing tetracycline resistance gene into the galactose operon as well as elements of phage λ including those elements responsible for cI repressor synthesis. C600 is available from the American Type Culture Collection, as ATCC Accession No. 23724.

Prototrophic strains of *Escherichia coli* which enable high level polypeptide expression even when grown in a minimal media are even more preferred as hosts for expression of genes encoding manganese superoxide dismutase. One presently preferred prototrophic strain is A4255. Strain A4255 containing the plasmid pMSE-4 has been deposited with the American Type Culture Collection under ATCC Accession No. 53250.

The resulting cells into which DNA encoding human manganese superoxide dismutase polypeptide or analog or mutant thereof has been introduced may be treated, e.g. grown or cultured as appropriate under suitable conditions known to those skilled in the art, so that the DNA directs expression of the genetic information encoded by the DNA, e.g. directs expression of the hMnSOD polypeptide or analog or mutant thereof, and the cell expresses the hMn-SOD polypeptide or analog or mutant thereof which may then be recovered.

As used throughout this specification, the term "superoxide dismutase" (SOD) means an enzyme or a polypeptide acting upon superoxide or oxygen-free radicals as receptors, or which catalyze the following dismutation reaction:

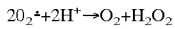

$$2O_2^- + 2H^+ \rightarrow O_2 + H_2O_2$$

The term "manganese superoxide dismutase" (MnSOD) as used herein means any superoxide dismutase molecule containing the element manganese, in any of its chemical forms.

The term "human manganese superoxide dismutase polypeptide" as used herein means a polypeptide of 198 amino acids a portion of the amino acid sequence of which is shown in FIG. 1; the N-terminus of the sequence is the lysine encoded by nucleotides 115–117 of FIG. 1 and the COOH terminus of the sequence is the lysine encoded by nucleotides 706–708 of FIG. 1.

The term "polypeptide manganese complex" as used herein means a molecule which includes a human manganese superoxide dismutase polypeptide in a complex with manganese in any of its chemical forms and which has the enzymatic activity of naturally-occurring human manganese superoxide dismutase.

The term "human manganese superoxide dismutase" as used herein means a molecule which includes at least two human manganese superoxide dismutase polypeptides in a complex with manganese in any of its chemical forms and which has the enzymatic activity of naturally-occurring human manganese superoxide dismutase.

The term "human manganese superoxide dismutase polypeptide analog" as used herein means a polypeptide which includes a human manganese superoxide dismutase polypeptide to either or both ends of which one or more additional amino acids are attached.

The term "polypeptide manganese complex analog" as used herein means a molecule which includes a polypeptide manganese complex, the polypeptide portion of which includes one or more additional amino acids attached to it at either or both ends.

The term "human manganese superoxide dismutase analog" as used herein means a molecule that includes at least two polypeptides at least one of which is human manganese superoxide dismutase polypeptide analog, in a complex with manganese in any of its chemical forms, and which has the enzymatic activity of naturally-occurring human manganese superoxide dismutase.

The term "human manganese superoxide dismutase polypeptide mutant" as used herein means a polypeptide having an amino acid sequence substantially identical to that of the human manganese superoxide dismutase polypeptide but differing from it by one or more amino acids.

The term "polypeptide manganese complex mutant" means a molecule which includes a human manganese superoxide dismutase polypeptide mutant in a complex with manganese in any of its chemical forms and which has the enzymatic activity of manganese superoxide dismutase.

The term "human manganese superoxide dismutase mutant" as used herein means a molecule which includes at least two polypeptides at least one of which polypeptides is a human manganese superoxide dismutase polypeptide mutant in a complex with manganese in any of its chemical forms and which has the enzymatic activity of naturally-occurring human manganese superoxide dismutase.

The mutants of hMnSOD polypeptide and hMnSOD which are included as a part of this invention may be prepared by mutating the DNA sequence shown in FIG. 1, the N-terminus of which sequence is the lysine encoded by nucleotides 115–117 and the COOH terminus of which sequence is encoded by nucleotides 706–708.

The DNA may be mutated by methods known to those of ordinary skill in the art, e.g. Bauer et al., Gene 37: 73–81 (1985). The mutated sequence may be inserted into suitable expression vectors as described herein, which are introduced into cells which are then treated so that the mutated DNA directs expression of the hMnSOD polypeptide mutants and the hMnSOD mutants.

The enzymatically active form of human manganese superoxide dismutase is believed to be a protein having at least two, and possibly four, identical subunits, each of which has approximately 198 amino acids in the sequence shown in FIG. 1 for human manganese superoxide dismutase, the N-terminus of the sequence being the lysine encoded by nucleotides 115–117 of FIG. 1 and the COOH terminus of the sequence being the lysine encoded by nucleotides 706–708 of FIG. 1.

Human MnSOD or analogs or mutants thereof may be prepared from cells into which DNA or cDNA encoding human manganese superoxide dismutase, or its analogs or mutants have been introduced. This human MnSOD or analogs or mutants may be used to catalyze the-dismutation or univalent reduction of the superoxide anion in the presence of protons to form hydrogen peroxide as shown in the following equation:

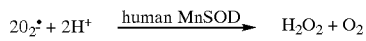

Veterinary and pharmaceutical compositions may also be prepared which contain effective amounts of hMnSOD or one or more hMnSOD analogs or mutant and a suitable carrier. Such carriers are well-known to those skilled in the art. The hMnSOD or analog or mutant thereof may be administered directly or in the form of a composition to the animal or human subject, e.g., to treat a subject afflicted by inflammations or to reduce injury to the subject by oxygen-free radicals on reperfusion following ischemia or organ transplantation. The hMnSOD or analog or mutant may also be added directly or in the form of a composition to the perfusion medium of an isolated organ, to reduce injury to an isolated organ by oxygen-free radicals on perfusion after excision, thus prolonging the survival period of the organ. Additionally, the hMnSOD or analog or mutant thereof may be used to reduce neurological injury on reperfusion following ischemia and to treat bronchial pulmonary dysplasia.

A method of producing enzymatically active human manganese superoxide dismutase or an analog or mutant thereof in a bacterial cell has also been discovered. The bacterial cell contains and is capable of expressing a DNA sequence encoding the human manganese superoxide dismutase or analog or mutant thereof. The method involves maintaining the bacterial cell under suitable conditions and in a suitable production medium. The production medium is supplemented with an amount of $Mn^{++}$ so that the concentration of $Mn^{++}$ in the medium is greater than about 2 ppm.

The bacterial cell can be any bacterium in which a DNA sequence encoding human manganese superoxide dismutase has been introduced by recombinant DNA techniques. The bacterium must be capable of expressing the DNA sequence and producing the protein product. The suitable conditions and production medium will vary according to the species and strain of bacterium.

The bacterial cell may contain the DNA sequence encoding the superoxide dismutase or analog in the body of a vector DNA molecule such as a plasmid. The vector or plasmid is constructed by recombinant DNA techniques to have the sequence encoding the SOD incorporated at a suitable position in the molecule.

In a preferred embodiment of the invention the bacterial cell is an *Escherichia coli* cell. A preferred auxotrophic strain of *E. coli* is A1645. A preferred prototrophic strain of *E. coli* is A4255 The *E. coli* cell of this invention contains a plasmid which encodes for human manganese superoxide dismutase or an analog or mutant thereof.

In a preferred embodiment of this invention, the bacterial cell contains the plasmid pMSE-4. A method of constructing this plasmid is described in the Description of the Figures and the plasmid itself is described in Example 2. This plasmid has been deposited with the ATCC under Accession No. 43250.

In another preferred embodiment of this invention, the bacterial cell contains the plasmid pMSΔRB4. A method of constructing this plasmid is described in the Description of the Figures and the plasmid itself is described in Example 5. This plasmid may be constructed from pSODβ₁T-11 which has been deposited with the American Type Culture Collection under Accession No. 53468.

In specific embodiments of the invention, an enzymatically active human manganese superoxide dismutase analog is produced by *E. coli* strain A4255 cell containing the plasmid p MSE-4 and by *E. coli* strain A4255 cell containing the plasmid pMSΔRB4.

The suitable production medium for the bacterial cell can be any type of acceptable growth medium such as casein hydrolysate or LB (Luria Broth) medium, the latter being preferred. Suitable growth conditions will vary with the strain of *E. coli* and the plasmid it contains, for example *E. coli* A4255 containing plasmid pMSE-4 is induced at 42° C. and maintained at that temperature from about 1 to about 5 hours. The suitable conditions of temperature, time, agitation and aeration for growing the inoculum and for growing the culture to a desired density before the production phase as well as for maintaining the culture in the production period may vary and are known to those of ordinary skill in the art.

The concentration of $Mn^{++}$ ion in the medium that is necessary to produce enzymatically active MnSOD will vary with the type of medium used.

In LB-type growth media Mn$^{++}$ concentrations of 150 ppm to 750 ppm have been found effective. It is preferred that in all complex types of growth mediums the concentration of Mn$^{++}$ in the medium is from about 50 to about 1500 ppm.

The specific ingredients of the suitable stock, culture, inoculating and production mediums may vary and are known to those of ordinary skill in the art.

This invention also concerns a method of recovering human manganese superoxide dismutase or analog or mutant thereof from bacterial cells which contain the same. The cells are first treated to recover a protein fraction containing proteins present in the cells including human manganese superoxide dismutase or analog or mutant thereof and then the protein fraction is treated to recover human manganese superoxide dismutase or analog or mutant thereof.

In a preferred embodiment of the invention, the cells are first treated to separate soluble proteins from insoluble proteins and cell wall debris and the soluble proteins are then recovered. The soluble proteins so recovered are then treated to separate, e.g. precipitate, a fraction of the soluble proteins containing the human manganese superoxide dismutase or analog or mutant thereof and the fraction is recovered. The fraction is then treated to separately recover the human manganese superoxide dismutase or analog or mutant thereof.

The following is a description of a more preferred embodiment of the invention. First, the bacterial cells are isolated from the production medium and suspended in a suitable solution having a pH of about 7.0 or 8.0. The cells are then disrupted and centrifuged. The resulting supernatant is heated for a period of about 30 to 120 minutes at a temperature between approximately 55 to 65° C., preferably for 45–75 minutes at 58 to 62° C. and more preferably one hour at 60° C., and then cooled to below 10° C., preferably to about 4° C. Any precipitate which may form during cooling is removed, e.g. by centrifugation and then the cooled supernatant is dialyzed against an appropriate buffer. Preferably the cooled supernatant is dialyzed by ultrafiltration employing a filtration membrane smaller than 30K, most preferably 10K. Appropriate buffers include 2 mM potassium phosphate buffer having a pH of about 7.8. After or simultaneously with this dialysis the cooled supernatant may optionally be concentrated to an appropriate volume, e.g. 0.03 of the supernatant's original volume has been found to be convenient. The retentate is then eluted on an anion exchange chromatography column with an appropriate buffered solution, e.g., a solution at least 20 mM potassium phosphate buffer having a pH of about 7.8. The fractions of eluent containing superoxide dismutase are collected, pooled and dialyzed against about 40 mM potassium acetate, pH 5.5. The dialyzed pooled fractions are then eluted through a cation exchange chromatography column having a linear gradient of about 40 to about 200 mM potassium acetate (KOAC) and a pH of 5.5. The peak fractions containing the superoxide dismutase are collected and pooled. Optionally the pooled peak fractions may then be dialyzed against an appropriate solution, e.g. water or a buffer solution of about 10 mM potassium phosphate having a pH of about 7.8.

The invention also concerns purified, i.e. substantially free of other substances of human origin, human manganese superoxide dismutase or analogs or mutants thereof produced by the methods of this invention. In particular, it concerns a human manganese superoxide dismutase analog having at least two polypeptides, at least one of which polypeptides has the amino acid sequence shown in FIG. 1, the N-terminus of which sequence is the lysine encoded by nucleotides 115–117 of FIG. 1 and the COOH terminus of which sequence is the lysine encoded by nucleotides 706–708 of FIG. 1 plus an additional methionine residue at the N-terminus (Met-hMnSOD). A preferred embodiment of this invention concerns purified Met-hMnSOD having a specific activity of 3500 units/mg.

The invention further concerns the ligation of human MnSOD gene fragments taken from various plasmids to yield a complete human MnSOD gene fragment which can be introduced into mammalian cells for the production of MnSOD. The various human MnSOD fragments isolated from the plasmids detail the nucleotide sequence of the genomic human MnSOD gene including coding and adjacent nucleotides as well as a restriction map and organization of the gene.

The genomic gene commences at nucleotide 479 which is the first nucleotide of the ATG starting codon and is underlined in FIG. 6. The TAA termination codon for the genomic gene is at nucleotides 2022–2024. These numbers are arbitrary numbers merely to assist in identifying the nucleotide region.

A restriction map and organization of the genomic human MnSOD gene is depicted in FIG. 5.

As noted, portions of genomic MnSOD DNA are found in each of three different clones, pMSG11-1, pMSG4, and pMSG-1b also depicted in FIG. 5 and the DNA from these clones was used to map the nucleotide sequence of FIG. 6.

Also shown in FIGS. 6 and 7 are the exon and intron regions of the human MnSOD gene.

This human MnSOD gene may be inserted into a plasmid which may in turn be inserted into a eucaryotic cell capable of expressing the human gene. Methods for recovery and purification of the protein are also contemplated similar to those discussed above.

EXAMPLES

The Examples which follow are set forth to aid in understanding the invention but are not intended to, and should not be construed to, limit its scope in any way. The Examples do not include detailed descriptions for conventional methods employed in the construction of vectors, the insertion of genes encoding polypeptides into such vectors or the introduction of the resulting plasmids into hosts. The Examples also do not include detailed description for conventional methods employed for assaying the polypeptides produced by such host vector systems or determining the identity of such polypeptides by activity staining of isoelectric focusing (IEF) gels. Such methods are well-known to those or ordinary skill in the art and are described in numerous publications including by way of example the following:

T. Maniatis, E. F. Fritsch and J. Sombrook, *Molecular Cloning: A Laboratory Manual,* Cold Spring Harbor Laboratory, New York (1982).

J. M. McCord and I. Fridovich, *J. Biol. Chem.* 244:6049–55 (1969).

C. Beauchamp and I. Fridovich, *Anal. Biochem.* 44:276–87 (1971).

Example 1

In order to identify MnSOD cDNA clones, mixed oligomer probes were synthesized according to the published amino acid sequence (18,19).

```
5'-probe - 30 mer sequence from AA15-AA24 (18,19)

5'                                              3'
TTGCATAATTTGTGCCTTAATGTGTGGTTC
        T    G    T    G
        G         G

3'-probe - 32 mer sequence from AA179-AA189 (18)

5'                                              3'
TCTGTTACGTTTTCCCAGTTTATTACGTTCCA
     G G              G G
```

The 5'-probe consisting of 30 nucleotides corresponds to amino acids 15 to 24 of mature MnSOD. The 3'-probe consisting of 32 nucleotides corresponds to amino acids 179 to 189 of mature MnSOD. The 5'-probe is a mixed probe consisting of 36 different sequences, as shown above. The 3'-probe is a mixed probe consisting of 16 different sequences as shown above. (When more than one nucleotide is shown at a given position, the DNA strand was synthesized with equimolar amounts of each of the shown nucleotides thus resulting in the mixed probe).

The 5'-probe was employed to screen 300,000 plaques of a T-cell cDNA library cloned into the gt-10 vector. Hybridization to phage plaque replicas immobilized on nitrocellulose filters was performed according to standard procedures (Maniatis et al. supra) except that the hybridization was performed at 50° C. in 8×SSC for 16 hrs. The filters were then washed at 50° C. with 5×SSC and 0.1% SDS. Three positive plaques were isolated and named Phi MS8, Phi MS1 and Phi MS1J.

EcoRI digests of DNA from Phi MS8 and Phi MS1 showed that they both have cDNA inserts approximately 800 bp long, which hybridize to both the 5' and 3' oligonucleotide probes. Phi MS1J carried only 450 bp cDNA insert which hybridized only to the 5' end probe.

The EcoRI inserts of the three phage clones were subcloned into the EcoRI site of pBR322 thus yielding pMS8-4, pMS1-4 and pMS1J, respectively. Restriction analysis and hybridization to the 5' and 3' oligonucleotide probes revealed similar patterns for both pMS8-4 and pMS1-4. The following restriction map showing the 5'→3' orientation has been deduced for both plasmids.

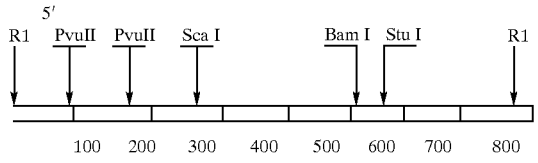

The sequence of the cDNA insert of pMS8-4 is shown in FIG. 1. The predicted amino acid sequence differs from the published amino acid sequence (19) in that Glu appears instead of Gln in three (3) locations (AA 42, 88, 108) and an additional two amino acids, Gly and Trp appear between $AA_{123-124}$ Sequence analysis of pMS1-4 and pMS1J revealed that the three MnSOD clones were independently derived and confirmed these differences from the published amino acid sequence.

The sequence upstream of the N-terminal Lysine of mature MnSOD predicts a pre-peptide sequence of 24 amino acids.

Example 2
Construction of pMSE-4: $Amp^R$ Human MnSOD Expression Plasmid

The starting point for the construction of pMSE-4 is the plasmid pMS8-4 which was obtained as described in Example 1. Plasmid pMS8-4, containing human MnSOD cDNA on an EcoRI insert, was digested to completion with NdeI and NarI restriction enzymes. The large fragment was isolated and ligated with a synthetic oligomer as depicted in FIG. 2. The resulting plasmid, pMS8-NN contains the coding region for the mature MnSOD, preceded by an ATG initiation codon. The above plasmid was digested with EcoRI, ends were filled in with Klenow fragment of Polymerase I and further cleaved with NdeI. The small fragment containing the MnSOD gene was inserted into $pSOD_\alpha 13$ which was treated with NdeI and NdeI. $pSOD_\alpha$ 13 may be obtained as described in pending, co-assigned U.S. patent application Ser. No. 644,245, filed Aug. 27, 1984 which is hereby incorporated by reference. This generated plasmid pMSE-4 containing the MnSOD coding region preceded by the cII ribosomal binding site and under the control of $\lambda.P_L$ promoter. Plasmid pMSE-4 has been deposited with the American Type Culture Collection under ATCC Accession No. 53250. All methods utilized in the above processes are essentially the same as those described in maniatis, supra.

Example 3
Expression of the Recombinant Human MnSOD

Plasmid pMSE-4 was introduced into *Escherichia coli* strain A4255 using known methods. Then the *E. coli* strain 4255, containing pMSE-4, were grown at 32° C. in Luria Broth (LB) medium containing 100 μg/ml of ampicillin until the Optical Density (OD) at 600 nm was 0.7. Induction was performed at 42° C. Samples taken at various time intervals were electrophoresed separated on sodium dodecyl sulfate-polyacrylamide gels electrophoresis (SDS-PAGE). The gels showed increases in human MnSOD levels up to 120 minutes post-induction, at which stage the recombinant MnSOD protein comprised 27% of total cellular proteins as determined by scanning of Coomassie-blue stained gel. Sonication of samples for 90 sec. in a W-375 sonicator and partitioning of proteins to soluble (s) and non-soluble (p) fractions by centrifugation at 10,000 g for 5 min. revealed that most of the recombinant MnSOD produced was non-soluble. The induced soluble protein fraction contained only slightly more SOD activity than the uninduced counterpart, as assayed by standard methods. See McCord et al., supra. Apparently a portion of the MnSOD found in the soluble fraction is inactive. This suggested that most of the human MnSOD produced under the conditions described in this Example is, in effect, inactive.

Example 4
Effect of $Mn^{++}$ in Growth Media on MnSOD Solubility and Activity

The addition of $Mn^{++}$ in increasing concentrations up to 450 ppm to the growth media of *E. coli* A4255, containing pMSE-4, prior to a 2 hr. induction at 42° C. had no adverse effect on the overall yield of human MnSOD. Analysis of sonicated protein fractions soluble (s) and non-soluble (p) on sodium dodecyl sulfate-polyacryl-amide gel electrophoresis (SDS-PAGE), showed increased solubilization of the recombinant protein with increased $Mn^{++}$ concentrations (Table 1). An assay of SOD activity (see McCord et al., supra) suggests a correlation between increased $Mn^{++}$ concentrations in the growth media and increased solubility of the MnSOD with an apparent optimum at 150 ppm $Mn^{++}$ concentration in the media (FIG. 3). Furthermore increased $Mn^{++}$ concentrations activated previously inactive soluble enzyme. Soluble protein fractions of induced cultures grown at these Mn$^{++}$ levels show up to 60-fold increase in SOD activity over soluble protein fractions of non-induced cultures grown at these Mn$^{++}$ levels. Activity staining of isoelectric focusing (IEF) gels (see Beauchamp et al, .) revealed that multi forms of the recombinant MnSOD were identical to those of native human liver MnSOD.

Results for human MnSOD production by *E. coli* A1645 containing pMSE-4 were similar to those described above.

TABLE 1

| Mn$^{++}$ (ppm) | Percent Soluble human Mn SOD of Total human MnSOD Induced | Percent Soluble human Mn SOD of Soluble Bacterial Proteins | Specific Activity units/mg Soluble Proteins |
|---|---|---|---|
| 0   | 30.6 | 7.2  | 30  |
| 50  | 72.7 | 15.4 | 241 |
| 100 | 78.0 | 16.9 | 356 |
| 150 | 82.9 | 18.8 | 606 |
| 200 | 82.0 | 20.8 | 338 |
| 250 | 79.2 | 20.4 | 380 |
| 300 | 80.8 | 20.3 | 381 |
| 450 | 89.2 | 22.4 | 323 |

Example 5

Construction of pMSΔRB4: Tet$^R$ Human MnSOD Expression Plasmid

Tet$^R$ expression vector, pΔRB, was generated from pSODβ$_1$T-11 by complete digestion with EcoRI followed by partial cleavage with BamHI restriction enzymes. pSODβ$_1$T-11 has been deposited with the American Type Culture Collection under Accession No. 53468. The digested plasmid was ligated with synthetic oligomer

5'-AATTCCOGGGTCTAGATCT-3'
3'-GGGCCCAGATCTAGACTAG-5' resulting in pΔRB containing the λP$_L$ promoter.

The EcoRI fragment of MnSOD expression plasmid pMSE-4, containing cII ribosomal binding site and the complete coding sequence for the mature enzyme, was inserted into the unique EcoRI site of pΔRB. The resulting plasmid, pMSΔRB4, contains the MnSOD gene under control of λPL and cII RBS and confers resistance to tetracycline (FIG. 4).

Example 6

Expression of Human MnSOD from pMS RB4

Plasmid pMSΔRB4 was introduced into *Escherichia coli* strain A4255, using known methods. Cultures were grown at 32° C. in Luria Broth (LB) containing various concentrations of Mn$^{++}$, until the Optical Density (OD) at 600 nm reached 6.7. Induction was performed at 42° C. Samples taken at various time intervals were electrophoresed on SDS-PAGE. hMnSOD level increased with induction time up to 120 minutes, at which stage it comprised about 15% of total cellular proteins as determined by scanning of Coomassie Blue stained gel.

The induced MnSOD was soluble, regardless of Mn$^{++}$ concentration in growth media. This is in contrast with observations for the Amp$^R$ plasmid pMSE-4. (See Example 4.) However, maximum SOD activity and expression level were dependent on Mn$^{++}$ supplementation (Table 2).

TABLE 2

MnSOD Expression in *E. coli* A4255 (pMS RB4)

| ppm Mn$^{++}$ | Percent Soluble hMnSOD of Soluble Bacterial Proteins | | Specific Activity Units/mg Soluble Proteins |
|---|---|---|---|
|  | 42° | 32° | 42° |
| 0   | 10.9 | 8.0  | 23  |
| 50  | 19.8 | 8.0  | 227 |
| 100 | 16.0 | 8.0  | 241 |
| 200 | 17.0 | 10.0 | 278 |
| 300 | 16.0 | 9.3  | 238 |

Example 7

Purification of Enzymatically Active Recombinant Human MnSOD

*E. coli* strain A4255 harboring plasmid pMS RB4 was fermented in LB supplemented with 750 ppm Mn$^{++}$, at 32° C. to an A600 of 17.0. Induction of human MnSOD expression was effected by a temperature shift to 42° C. for 2 hours at which stage the culture reached A600 of 43.0. Cells were harvested by centrifugation and resuspended in 0.2 original volume in 50 mM potassium phosphate buffer, pH 7.8 containing 250 mM NaCl. Bacteria were disrupted by a double passage through Dynomill, centrifuged and cell debris were discarded. The supernatant was heated for 1 hour at 60° C., cooled to 40° C. and the cleared supernatant was concentrated to 0.03 original volume and dialyzed against 2 mM potassium phosphate buffer, pH 7.8, on a Pelicon ultra filtration unit equipped with a 10K membrane. The crude enzyme preparation was loaded onto a DE52 column, washed thoroughly with 2 mM potassium phosphate buffer, pH 7.8 and eluted with 20 mM potassium phosphate buffer, pH 7.8. Pooled fractions containing the enzyme were dialyzed against 40 mM potassium acetate, pH 5.5, loaded onto a CM52 column and eluted with a linear gradient of 40–200 mM potassium acetate, pH 5.5. Peak fractions containing human MnSOD were pooled, dialyzed against H$_2$O, adjusted to 10 mM potassium phosphate buffer, pH 7.8 and frozen at −20° C.

Recombinant human MnSOD obtained was more than 99% pure, with a specific activity of about 3500 units/mg. The overall yield of the purification procedure was about 30% (Table 3).

Sequencing of the purified enzyme shows the presence of an additional methionine at the N-terminal amino acid as compared with the known human MnSOD (19).

Analysis for metal content by atomic absorption revealed about 0.77 atoms Mn per enzyme subunit. This is in accordance with published data (23).

TABLE 3

Purification of Recombinant Human* Mn-SOD

| Step | Total Proteins gm | Yield gmSOD | Yield % | Specific Activity units/mg |
|---|---|---|---|---|
| Dynomill supernatant | 100.0 | 11.9 | 100.0 | 417 |
| 60° C. supernatant | 24.0 | 8.2 | 68.9 | 1197 |
| Pelicon retentate | 20.0 | 7.5 | 63.0 | 1350 |

TABLE 3-continued

Purification of Recombinant Human* Mn-SOD

| Step | Total Proteins gm | Yield gmSOD | % | Specific Activity units/mg |
|---|---|---|---|---|
| DE52 eluate | 7.3 | 5.7 | 48.0 | 2732 |
| CM52 eluate | 4.2 | 4.2 | 35.3 | 3500 |

*values for enzyme purified from 15 L fermentation.

Example 8
Isolation and Structure of Human MnSOD Gene

Human placental DNA digested with HindIII and BamHI was fractionated according to its size, hybridized with an MnSOD cDNA probe and the positive enriched fractions were cloned in pBR322. Three distinct clones were identified according to their restriction and hybridization patterns: pMSG11-1, overlapping pMSG4, both comprising the 5' end of MnSOD gene and followed by the consecutive clone pMSG-1b which contains the 3' end of the gene. Plasmid pMSG11-1 has been deposited in the ATCC under Accession No. 67363; plasmid pMSG4 has been deposited in the ATCC under Accession No. 67364; and plasmid pMSG-1b has been deposited in the ATCC under Accession No. 67365. FIG. 5 shows the restriction map and organization of the MnSOD gene. The nucleotide sequence of the gene is shown in FIG. 6. The MnSOD gene spans a region of about 15 Kb and contains six exons. The first intron interrupts the region coding for the leader peptide while the last intron appears in the 3' untranslated region downstream to the TAA termination codon.

The sequences of the donor and acceptor splice junctions at the exon-intron boundries are summarized in FIG. 7 and compared with the consensus sequence. It should be pointed out that the first intron contains either an unusual donor sequence; GG instead of the highly conserved GT (as depicted in FIG. 6), or an unusual acceptor sequence; GG instead of AG (if one moves the exon by one nucleotide). All other four introns are bound by the conserved GT . . . AG nucleotides.

The promoter region lacks TATA and/or CAT boxes. However, it is highly rich in GC and contains eight repeats of the consensus hexanucleotide core for binding transcription factor Spl (GGGCGG). Moreover, it includes a series of direct repeats and possible stem-loop structures. The polyadenylation signal AATAAA appears 85 nucleotides downstream from the last exon (according to the known cDNA sequence). The sequence of the promoter region and the sequence of the coding regions and adjacent nucleotides was determined.

The MnSOD gene regions from plasmids pMSG11-1, pMSG4 and pMSG-1b can be conveniently isolated from the plasmids and ligated to one another to form the entire MnSOD gene. For example, the approximately 6 KB HindIII-partial BamHI fragment from pMSG11-1 can be ligated to the entire BamHI insert in plasmid pMSG4 followed by ligation to the entire BamHI insert from pMSG-1b. The result of this ligation would be a DNA fragment encoding the human MnSOD gene. This DNA fragment could then be introduced into mammalian cells through known methods either directly or after ligation to a cloning vehicle such as a plasmid or virus. The transformed cell line could then be used for production of MnSOD polypeptide, analog or mutant thereof, by culturing in a suitable medium under suitable conditions. The polypeptide so produced could then be recovered by methods similar to those set forth in Example 7. The polypeptide so recovered could then be used formulated and used therapeutically, for example, for treatment of ischemia or inflammation.

Example 9
Transcription of MnSOD in Human Cells

The human MnSOD cDNA from plasmid pMS-84 (FIG. 2) was hybridized to polyA$^+$ RNA from human cell lines, human placenta, mouse WEHI-3 cells and bovine liver. Two species of human mRNA for MnSOD were identified, a major transcript of human mRNA encoding MnSOD of about 1000 nucleotides (nt) long and a minor transcript of about 4000 nt in length. The mouse mRNA for MnSOD is similar in size to the human major transcript, whereas mRNA for bovine MnSOD is about 300 nt longer. The long human transcript (4000 nucleotides) hybridizes to the fifth intron of the human MnSOD gene, downstream from the exon coding for the carboxy terminus of the enzyme. This partially spliced transcript is non-tissue specific.

The proportion of both CuZn and MnSOD mRNAs in various cell lines was in the order of $10^{-3}$%, as determined by hybridization of the SOD cDNA probes to dot blots of serially diluted polyA$^+$ RNA (Table IV). The MnSOD message was most abundant in Hepatoma cells ($2.5 \times 10^{-3}$%) and CuZn SOD transcripts were most abundant in the T-lymphocyte line ($4 \times 10^{-3}$%).

TABLE IV

Transcription Levels of MnSOD and CuZn SOD in Human Cell Lines
% of polyA$^+$ RNA

| Cell Line | MnSOD | CuZnSOD |
|---|---|---|
| 1. PEER T-cell | $0.6 \times 10^{-3}$ | $4.0 \times 10^{-3}$ |
| 2. 5637 Bladder Carcinoma | $0.8 \times 10^{-3}$ | $1.6 \times 10^{-3}$ |
| 3. Alexander Hepatoma | $2.5 \times 10^{-3}$ | $2.0 \times 10^{-3}$ |

Example 10
Pharmacokinetic and Anti-Inflammatory Properties of Human Recombinant Human MnSOD Introduction The anti-inflammatory activity of CuZn SOD has been demonstrated in various biological models. The pharmokinetics of CuZn SOD after administration by various routes has also been examined, and it has been found to have a relatively short half-life (approximately 7 minutes when injected intravenously). By contrast, very little is known about the pharmacokinetics and biological activity of MnSOD. There is only one report on the comparison of the pharmokinetic and anti-inflammatory properties of the CuZn and the Mn containing enzymes (Baret et al., 1984). Baret et al. claim that the half-life of MnSOD injected intravenously is extremely long (6.45 hours). On the other hand, MnSOD was shown to be ineffective against carrageenan-induced paw inflammation in rats, while the CuZn SOD was effective in reducing inflammation. In the study described herein, we have compared the pharmacokinetic properties of recombinant human MnSOD with that of a recombinant human CuZn SOD analog when given subcutaneously. Concurrently, we have compared the anti-inflammatory activities of these two enzymes in the carrageenan paw edema model. Unexpectedly, it was found that MnSOD was efficacious in reducing inflammation in the rat model system.

Pharmacokinetic Studies

Rats were injected subcutaneously with 50 mg/kg body weight of either recombinant human CuZn SOD analog or recombinant human MnSOD. Blood samples were drawn 0.5, 2, 4, 8, 24, 30 and 48 hours after injection and superoxide dismutase activity in the samples was determined by an enzymatic assay (Fridovich).

FIG. 8 summarizes the results. As shown, CuZn SOD analog values reached a maximum of about 10 ug/ml after 2 hours and stayed at about that level for additional 6 hours, but dropped to pre-injection levels after 24 hours. By contrast, MnSOD levels gradually increased to reach a maximal level of about 70 ug/ml by 8 hours, and stayed at about this level for at least 30 hours. By 48 hours, the enzyme activity in serum dropped to about 20 ug/ml, a value that was still well above the pre-injection levels.

Anti-Inflammatory Activity

The rat model of carrageenan-induced paw edema was used to assay the anti-inflammatory activity of CuZn SOD analog and MnSOD. In this model, Wistar-derived male rats (130–150g b.w.) were given a sub-plantar injection of 0.1 ml of 0.1% w/v carrageenan into the left hind paw. The paw volume was measured by an Hg-displacement volumeter (a modification of a Ugo-Basile volumeter, Camerio, Italy) before and at hourly intervals after paw injection. Animals were divided into 4 groups (8 rats/group). One group received a subcutaneous injection of 50 mg/kg of MnSOD 24 hours before carrageenan administration (−24 h Mn; cf. FIG. 9). The second group was injected with Cu/Zn SOD analog (50 mg/kg) 24 hours before the carrageenan challenge (−24 h Cu), while the third group was injected with 60 mg/Kg of CuZn SOD analog only 2 hours before the challenge (−2 h Cu). The fourth group did not receive any pretreatment and served as a control.

The results are shown in FIG. 9. As seen, the administration of CuZn SOD analog 2 hours before the induction of inflammation resulted in a 50% reduction of the swelling response. In contrast, pretreatment with the CuZn enzyme 24 hours before challenge was without effect. However, a 24-hour pretreatment with MnSOD resulted in an anti-inflammatory response which was similar to the effect of the 2 hours pretreatment with CuZn SOD analog.

Conclusions

It has been demonstrated herein that the rate of disappearance of recombinant human MnSOD in the rat is much lower than that of the recombinant CuZn SOD analog. This is in agreement with the previous report of Baret et al. (1984) concerning the natural human MnSOD. However, the manganese-containing enzyme has been shown herein to be active in vivo as an anti-inflammatory agent—an activity that is attributed to its superoxide dismutase ability. This finding is surprising in view of the report of Baret et al. (1984), which claimed that MnSOD was not active in a similar system. The finding that MnSOD remains efficacious as an anti-inflammatory drug even 24 hours after administration indicates that it may be used as a long-acting therapeutic agent.

REFERENCES

1. McCord, M. and Fridovich, I., J. Biol. Chem. 244: 6049–55 (1969).
2. Fridovich, I. in *Advances in Inorganic Biochemistry*, eds. Eichhorn, G. L. and Marzilli, L. G. (Elsevier/North Holland, New York), pp. 67–90 (1979).
3. Freeman, B. A. and Crapo, J. D., Laboratory Investion 47: 412–26 (1982).
4. Steinman, H. M. in *Superoxide Dismutase,* ed. Oberley, L. W. (CRC Press, Florida), pp. 11–68 (1982).
5. Hartz, J. W. and Deutsch, H. F., J. Biol. Chem. 247: 7043–50 (1972).
6. Jabusch, J. R., Farb, D. L., Kerschensteiner, D. A. and Deutsch, H. P., Biochemistry 19: 2310–16 (1980).
7. Barra, D., Martini, F., Bannister, J. V., Schinina, M. W., Rotilio, W. H., Bannister, W. H. and Bossa, F., FEBS Letters 120: 53–56 (1980).
8. Lieman-Hurwitz, J., Dafni, N., Lavie, V. and Groner, Y., Proc. Natl. Acad. Sci. USA 79: 2808–11 (1982).
9. Sherman, L., Dafni, N., Lieman-Hurwitz, J. and Groner, Y., Proc. Natl. Acad. Sci. USA 80: 5465–69 (1983).
10. Oberley, L. W. and Buettner, G. R., Cancer Research 39; 1141–49 (1979).
11. Huber, W. and Menander-Huber, K. B., Clinics in Rheum. Dis. 6: 465–98 (1980).
12. McCord, J. M. and Roy, R. S., Can. J. Physiol. Pharma. 60: 1346–52 (1982).
13. Alvarez, J. G. and Storey, B. T., Biol. Reprod. 28: 1129–36 (1983).
14. Talmasoff, J. M., Ono, T. and Cutler, R. G., Proc. Natl. Acad. Sci. USA 77: 2777–81 (1980).
15. Lowry, O. H. Rosebrough, N. J., Farr, A. L. and Randall, R. J., J. Biol. Chem. 193: 265–75 (1951).
16. Weser, U. and Hartmann, H. J., FEBS Letters 17: 78–80 (1971).
17. Jewett, S. LO., Latrenta, G. S. and Beck, C. M., Arc. Biochem. Biophys. 215: 116–128 (1982).
18. Harris, J. I. and Steinman, H. M., *Superoxide and Superoxide Dismutase,* Michelson, A. M., McCord, J. M. and Fridovich, I. eds., Academic Press, London, pp. 225–230 (1977).
19. Barra, D., Schinina, M. E., Simmaco, M., Bannister, J. V., Bannister, W. H., Rotilio, G. and Bossa, F., J. Biol. Chem. 259: 12595–601 (Oct. 25, 1984).
20. Baret, A., Jadot, G., and Michelson, A. M., Biochemical Pharmacology 33: 2755–60 (Sep. 1, 1984).
21. McCord, J. M. and Salin, M. L., *Movement, Metabolism and Bactericidal Mechanisms of Phagocytes,* Ross, A., Patriarca, P. L., Romeo, D. (eds) pp. 257–264 (1977).
22. Touati, D., Journal of Bacteriology 155: 1078–87 (1983).
23. McCord, J. M., Boyle, J. A., Day, Jr., E. D., Rizzolo, L. J. and Salin, M. L., *Superoxide and Superoxide Dismutase,* Michaelson, A.M., McCord, J. M., and Fridovich, I. (eds) Academic Press, London pp. 129–138 (1977).
24. European Patent Publication No. 0131843 A1, published Jan. 23, 1985, corresponding to European Patent Application No. 84107717.5, filed Jul. 3, 1984, which claims priority of U.S. Ser. No. 514,188, filed Jul. 15, 1983.
25. Hallewell, et al., Nucleic Acids Res. 5: (1985).
26. European Patent Publication 0138111 A1, published Apr. 24, 1985, corresponding to European Patent Application No. 84111416.8, filed Sep. 25, 1984, which claims priority of U.S. Ser. No. 538,607, filed Oct. 3, 1983, and U.S. Ser. No. 609,412, filed May 11, 1984.
27. EMBO Journal 4(1): 77–84 (January 1985).
28. Abstracts of the Fourth International Conference on Superoxide and Superoxide Dismutase, Rome, Italy, Sep. 1–6, 1985.

What is claimed is:

1. A method of treating a subject afflicted with inflammation which comprises administering to the subject an effective amount of a recombinant polypeptide having an amino acid sequence substantially identical to that of human superoxide dismutase.

2. A method of reducing injury to a subject occurring upon reperfusion following ischemia which comprises administering to the subject an effective amount of a recombinant polypeptide having an amino acid sequence substantially identical to that of human manganese superoxide dismutase.

3. A method of prolonging the survival period of an isolated organ which comprises adding an effective amount of a recombinant polypeptide having an amino acid sequence substantially identical to that of human superoxide dismutase to the perfusion medium of the isolated organ.

4. A method of treating a subject afflicted with bronchial pulmonary dysplasia which comprises administering to the subject an effective amount of a recombinant polypeptide having an amino acid sequence substantially identical to that of human manganese superoxide dismutase.

* * * * *